US010573200B2

(12) United States Patent
Caron et al.

(10) Patent No.: US 10,573,200 B2
(45) Date of Patent: Feb. 25, 2020

(54) SYSTEM AND METHOD FOR DETERMINING A POSITION ON AN EXTERNAL SURFACE OF AN OBJECT

(71) Applicant: CAE HEALTHCARE CANADA INC., Saint-Laurent (CA)

(72) Inventors: Francois Caron, Saint-Laurent (CA); Jean-Sebastien Flamand, Saint-Laurent (CA)

(73) Assignee: CAE HEALTHCARE CANADA INC., Saint-Laurent, Quebec (CA)

( * ) Notice: Subject to any disclaimer, the term of this patent is extended or adjusted under 35 U.S.C. 154(b) by 490 days.

(21) Appl. No.: 15/473,896

(22) Filed: Mar. 30, 2017

(65) Prior Publication Data

US 2018/0286283 A1  Oct. 4, 2018

(30) Foreign Application Priority Data

Mar. 30, 2017 (CA) .................................. 2962780

(51) Int. Cl.
*G09B 23/28* (2006.01)
*A61B 8/00* (2006.01)

(52) U.S. Cl.
CPC .......... *G09B 23/286* (2013.01); *A61B 8/4254* (2013.01); *A61B 8/461* (2013.01); *A61B 8/54* (2013.01); *A61B 8/565* (2013.01)

(58) Field of Classification Search
None
See application file for complete search history.

(56) References Cited

U.S. PATENT DOCUMENTS 7,339,586 B2 * 3/2008 Guhring .................... G06T 7/30
   345/424
8,721,344 B2    5/2014 Marmaropoulos et al.
(Continued)

FOREIGN PATENT DOCUMENTS

WO    2007101346 A1    9/2007

OTHER PUBLICATIONS

Wang, Yang & Georgescu, Bogdan & Chen, Terrence & Wu, Wen & Wang, Peng & Lu, Xiaoguang & Ionasec, Razvan & Zheng, Yefeng & Comaniciu, Dorin."Learning-Based Detection and Tracking in Medical Imaging: A Probabilistic Approach." (2013). (Year: 2013).*

(Continued)

*Primary Examiner* — Roy Y Yi
(74) *Attorney, Agent, or Firm* — Fasken Martineau Dumoulin LLP

(57) ABSTRACT

The present system and method determine a position on an external surface of an object. The system comprises a magnetic field measurement module and an ultrasound measurement module. A control unit stores a magnetic field map of the object comprising a first plurality of reference areas of the external surface of the object and associated reference magnetic field value. The control unit also stores an ultrasound map of the object comprising a second plurality of reference areas of the external surface of the object and associated reference ultrasound characteristic. The processing unit determines: a subset of the reference areas for which the associated reference magnetic field value is substantially equal to a measured magnetic field value, a subset of the reference areas for which the associated reference ultrasound characteristic is substantially equal to a measured ultrasound characteristic, and determines the position on the external surface of the object.

12 Claims, 13 Drawing Sheets

(56) References Cited

U.S. PATENT DOCUMENTS

| | | |
|---|---|---|
| 9,827,448 B2 * | 11/2017 | Barnes .................... A61N 7/02 |
| 2012/0076371 A1 | 3/2012 | Caruba et al. |
| 2012/0238875 A1 | 9/2012 | Savitsky et al. |
| 2013/0079627 A1 | 3/2013 | Lee |
| 2014/0257080 A1 | 9/2014 | Dunbar et al. |
| 2015/0056591 A1 | 2/2015 | Tepper et al. |

OTHER PUBLICATIONS

Bø, Lars Eirik & Gjerald, Sjur & Brekken, Reidar & Tangen, Geir & Hernes, Toril, "Efficiency of ultrasound training simulators: Method for assessing image realism. Minimally invasive therapy & allied technologies", 2010, MITAT : official journal of the Society for Minimally Invasive Therapy. (Year: 2010).*

* cited by examiner

SYSTEM AND METHOD FOR DETERMINING A POSITION ON AN EXTERNAL SURFACE OF AN OBJECT

TECHNICAL FIELD

The present disclosure relates to the field of medical simulation procedures, and more specifically to a system and method for determining a position on an external surface of an object.

BACKGROUND

In the context of medical simulation procedures, a simulated medical instrument (or a real medical instrument adapted for performing medical simulations) is used for performing medical simulation procedures, for example on a patient simulator simulating a patient or on a real patient.

For example, to simulate ultrasound based medical procedures, a simulation apparatus including an ultrasound probe is used. The simulation apparatus generates ultrasound images of an anatomic region of a patient simulator or a real patient where the ultrasound probe is located, and the ultrasound images are displayed on a screen.

The simulation apparatus including the ultrasound probe is positioned adjacent to an area of an external surface of the object under examination (patient simulator or real patient). The ultrasound images are representative of a region located inside the object under examination and bellow the area of the external surface faced by the ultrasound probe. The ultrasound probe, the area of the external surface and the region inside the object are substantially aligned.

In the case where the external surface of the object under examination includes a plurality of areas of interest, each of the areas of interest is a candidate for being scanned by the ultrasound probe. Knowing the position of the ultrasound probe with respect to these areas of interest may be an important factor for the medical procedure being simulated. However, the simulation apparatus including the ultrasound probe does not necessarily include appropriate means for determining this position.

There is therefore a need for a new system and method for determining a position on an external surface of an object.

SUMMARY

According to a first aspect, the present disclosure relates to system for determining a position on an external surface of an object. The system comprises an apparatus, a control unit, and a processing unit. The apparatus comprises a magnetic field measurement module for measuring a magnetic field value induced by the object. The apparatus also comprises an ultrasound measurement module for generating an ultrasound signal, receiving a corresponding reflected ultrasound signal reflected by the object, and measuring an ultrasound characteristic of the reflected ultrasound signal. The control unit comprises memory for storing a magnetic field map and an ultrasound map of the object. The magnetic field map comprises a first plurality of reference areas of the external surface of the object, each one of the first plurality of reference areas having an associated reference magnetic field value. The ultrasound map comprises a second plurality of reference areas of the external surface of the object, each one of the second plurality of reference areas having an associated reference ultrasound characteristic. The processing unit determines a subset of the first plurality of reference areas for which the associated reference magnetic field value is substantially equal to the measured magnetic field value. The processing unit further determines a subset of the second plurality of reference areas for which the associated reference ultrasound characteristic is substantially equal to the measured ultrasound characteristic. The processing unit also correlates the subset of the first plurality of reference areas and the subset of the second plurality of reference areas to determine the position on the external surface of the object.

According to a second aspect, the present disclosure relates to a method for determining a position on an external surface of an object. The method comprises storing by a memory of a control unit a magnetic field map of the object, the magnetic field map comprising a first plurality of reference areas of the external surface of the object, each one of the first plurality of reference areas having an associated reference magnetic field value. The method further comprises storing by the memory of the control unit an ultrasound map of the object, the ultrasound map comprising a second plurality of reference areas of the external surface of the object, each one of the second plurality of reference areas having an associated reference ultrasound characteristic. The method also measures by a magnetic field measurement module of an apparatus a magnetic field value induced by the object, generates by an ultrasound measurement module of the apparatus an ultrasound signal, receives by the ultrasound measurement module of the apparatus a corresponding reflected ultrasound signal reflected by the object, and measures by the ultrasound measurement module of the apparatus an ultrasound characteristic of the reflected ultrasound signal. The method then determines by a processing unit of the control unit a subset of the first plurality of reference areas for which the associated reference magnetic field value is substantially equal to the measured magnetic field value, determines a subset of the second plurality of reference areas for which the associated reference ultrasound characteristic is substantially equal to the measured ultrasound characteristic, and correlates the subset of the first plurality of reference areas and the subset of the second plurality of reference areas to determine the position on the external surface of the object.

BRIEF DESCRIPTION OF THE DRAWINGS

Embodiments of the disclosure will be described by way of example only with reference to the accompanying drawings, in which.

DETAILED DESCRIPTION

The foregoing and other features will become more apparent upon reading of the following non-restrictive description of illustrative embodiments thereof, given by way of example only with reference to the accompanying drawings. Like numerals represent like features on the various drawings.

Various aspects of the present disclosure generally address one or more of the problems related to the determination of a position on an external surface of an object through correlations of collected data, where the data are collected via at least two different measurement technologies.

Figure 1:
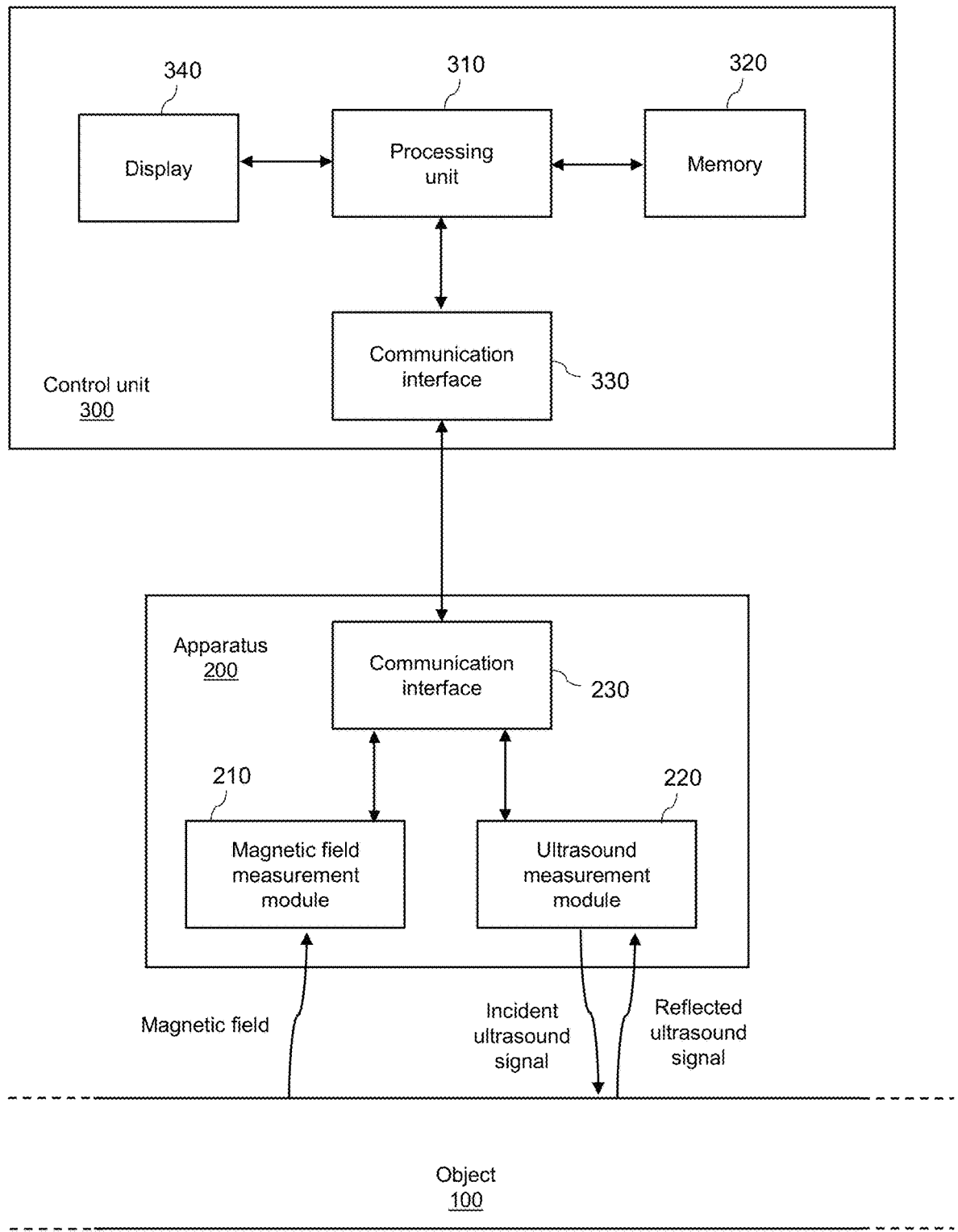
FIG. 1 illustrates a system for determining a position on an external surface of an object.

Referring now to FIG. 1, a system 10 for determining a position on an external surface of an object 100 is represented.

The system 10 comprises an apparatus 200 for collecting data related to the object 100, and a control unit 300 for processing the data collected by the apparatus 200.

The apparatus 200 comprises a magnetic field measurement module 210 for measuring a magnetic field or variation of magnetic field, hereinafter referred as a magnetic field value, generated or induced by the object 100.

The apparatus 200 also comprises an ultrasound measurement module 220 for generating an incident ultrasound signal, receiving a corresponding reflected ultrasound signal reflected by the object 100, and measuring an ultrasound characteristic of the reflected ultrasound signal.

The system 10 is used in the context of simulations of medical procedures, or in the context of real medical procedures. The object 100 may be a simulator of a patient for simulating a medical procedure. For example, the object 100 is patient simulator simulating a human body, or at least part(s) of a human body (e.g. only the head, only the torso, etc.). Alternatively, the object 100 is a real patient attending a real medical procedure, or a person involved in the simulation of a medical procedure.

The apparatus 200 may be a real medical instrument or a mock-up of a medical instrument. For example, the apparatus 200 is an ultrasound device used for medical procedures, which includes by default the ultrasound measurement module 220. The ultrasound device 200 has been adapted to also include the magnetic field measurement module 210. Alternatively, the apparatus may be a mock-up ultrasound device, based on an ultrasound device used for performing medical procedures.

The apparatus 200 may include at least one of the following optional components (not represented in FIG. 1): a processor, a memory, a display, etc. The display (e.g. a regular screen or a touchscreen) displays at least one of the measured magnetic field value and the measured ultrasound characteristic. The processor and memory process at least one of the measured magnetic field value and measured ultrasound characteristic, before transmission by the communication interface 230. For example, the processor and memory generate a calibrated magnetic field value (and/or calibrated ultrasound characteristic) based on the measured magnetic field value (and/or measured ultrasound characteristic) and calibration data stored in the memory. The calibrated magnetic field (and/or calibrated ultrasound characteristic) is transmitted by the communication interface 230 to the control unit 300. Generation of the calibrated magnetic field and/or calibrated ultrasound characteristic further takes into consideration whether the apparatus is used with a patient or a patient simulator.

The communication interface 230 implements a wireless communication technology (e.g. Wi-Fi, Bluetooth®, etc.) for exchanging data with the control unit 300. Alternatively or complementarily, the communication interface 230 implements a wired communication technology.

The control unit 300 includes a communication interface 330 for exchanging data with the apparatus 200. The communication interface 330 implements at least one of a wireless and a wired communication technology.

The control unit 300 includes a processing unit 310 and memory 330. The processing unit 310 has one or more processors (not represented in FIG. 1 for simplification purposes) capable of executing instructions of computer program(s). Each processor may further have one or several cores. The memory 320 stores instructions of the computer program(s) executed by the processing unit 310, data generated by the execution of the computer program(s), data received via the communication interface 330 (e.g. the measured magnetic field value and the measured ultrasound characteristic transmitted by the apparatus 200), etc. The control unit 300 may comprise several types of memories, including volatile memory, non-volatile memory, etc.

The processing unit 310 executes a program implementing an algorithm for determining a position on the external surface of the object 100, based on the measured magnetic field value and the measured ultrasound characteristic received from the apparatus 200.

The control unit 300 may be involved in the simulation of a plurality of medical procedures, and the determination of the position on the external surface of the object 100 is only one among several simulation functionalities implemented by the control unit 300.

The control unit 300 comprises a display 340 for displaying data generated by the processing unit 310 (e.g. anatomical representation corresponding to the position and orientation of the ultrasound measurement module 220 on the external surface of the object 100), data received via the communication interface 330 (e.g. the measured magnetic field value and the measured ultrasound characteristic transmitted by the apparatus 200), physiological model corresponding to the position and orientation of the ultrasound measurement module 220 for the simulation performed, etc.

In an alternative embodiment, the control unit 300 does not include the display 340, and the control unit 300 rather communicates through the communication interface 330 with a remote electronic device which comprises a display to display the data generated by the processing unit 310 as described above.

The control unit 300 may also include a user interface (not represented in FIG. 1) for allowing a user to interact with the control unit 300.

Although shown as two separate entities, the apparatus 200 and the control unit 300 could be embedded within a single device, in which case, the magnetic field measurement module 210 and the ultrasound measurement module 220 communicate directly with the processing unit 310.

Figure 2:
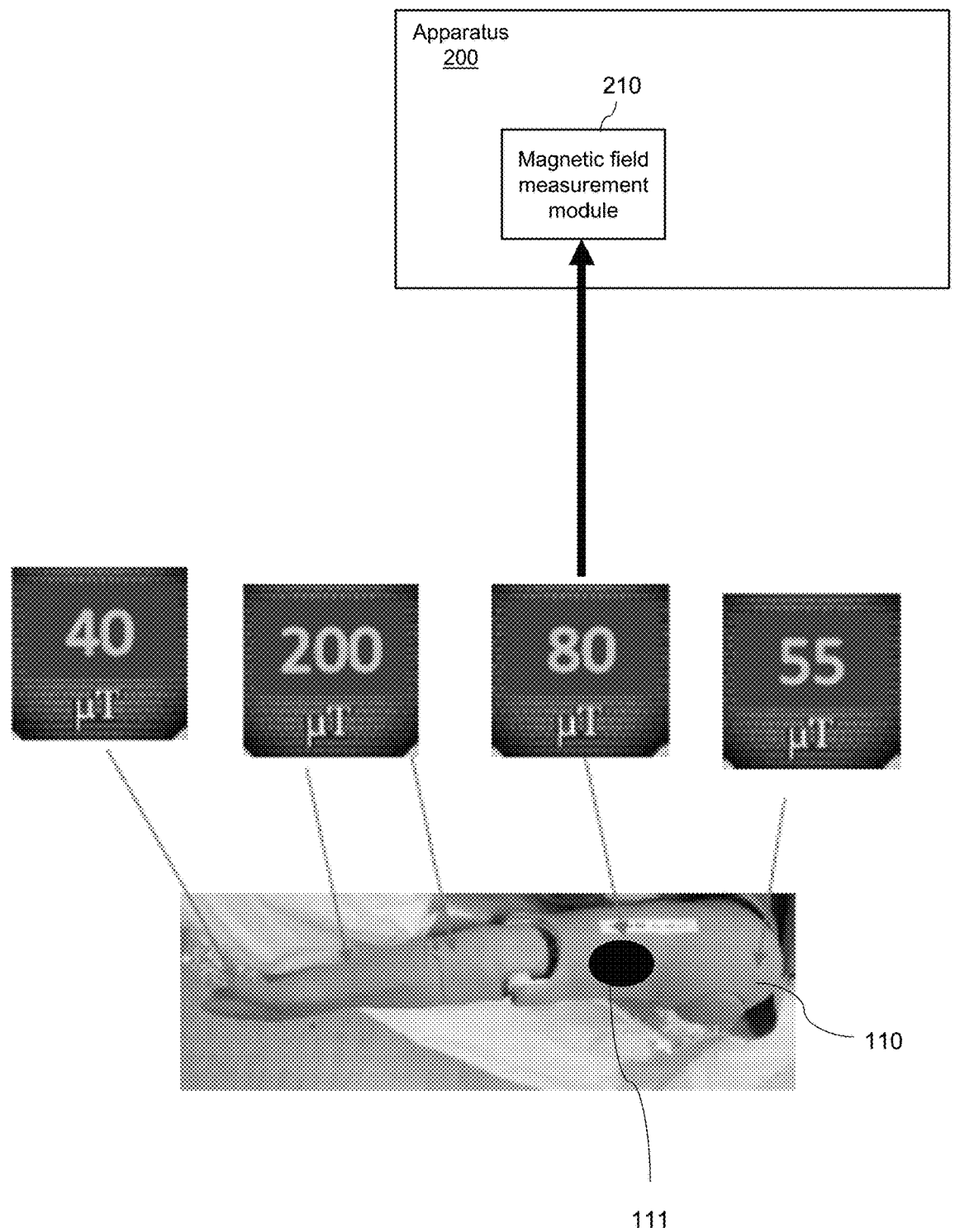
FIG. 2 illustrates operations of a magnetic field measurement module of the system represented in FIG. 1.

Reference is now made concurrently to FIGS. 1 and 2. FIG. 2 illustrates the operations of the magnetic field measurement module 210 of the apparatus 200.

For illustration purposes, the object 100 is either a human or a patient simulator used for simulation procedures, and the object 100 comprises an arm 110 represented in FIG. 2. When the apparatus 200 is located at different positions with respect to the arm 110, the magnetic field measurement module 210 measures different values of the magnetic field, which depend on the current position of the apparatus 200 with respect to the arm 110.

As illustrated in FIG. 2, if the apparatus 200 is moved longitudinally along the arm 110 from one extremity (the hand) to the other extremity (the shoulder), the magnetic field value measured by the magnetic field measurement module 210 takes the following values: 40 µT (micro Tesla), 200 µT, 80 µT and 55 µT.

More generally, when the apparatus 200 is positioned adjacent to an area (e.g. 111) of the surface of the object 100, the magnetic field measurement module 210 measures a magnetic field value (e.g. 80 µT) generated or induced by the object 100 and corresponding to the area of the object 100. The orientation of the apparatus 200, as well as the distance between the apparatus 200 and the area 111 of the surface of the object 100, may vary. FIG. 2 is a schematic representation of the apparatus 200, and the size of the apparatus 200 with respect to the size of the arm 110 is not realistic.

Furthermore, the apparatus 200 may be positioned adjacent to an area (e.g.111) of the surface of the object 100, and the magnetic field measurement module 210 measures a variation of the magnetic field generated or induced by the object 100 upon movement of the magnetic field measurement module 210 upon movement adjacent to the object 100.

Magnetic field measurement modules 210 are well known in the art, and can have various form factors adapted for being integrated in various types of apparatus 200. The magnetic field measurement module 210 outputs the measured magnetic field value, which is directly transmitted by the communication interface 230 of the apparatus 200. As previously mentioned, the measured magnetic field value may correspond to a discrete magnetic field measurement, or to a variation of magnetic field over an area. Alternatively, the magnetic field measurement module 210 outputs the measured magnetic field value, which is processed (e.g. calibrated) before transmission by the communication interface 230 of the apparatus 200.

In the case where the object 100 is a human, the magnetic field measured by the magnetic field measurement modules 210 corresponds and depends on the portion of the human body adjacent to the apparatus 200 (each portion of the human body generating a different electrical activity, which in turns generates a corresponding magnetic field).

In the case where the object 100 is a patient simulator simulating a human, a material or an electronic component having specific magnetic properties can be used for artificially generating different magnetic fields at different locations of the patient simulator. Examples of material or electronic component having specific magnetic properties include: metal, magnets, electromagnets, electronic component(s), RFID tags or any other known component or material generating or inducing an electromagnetic signal.

Figure 3:
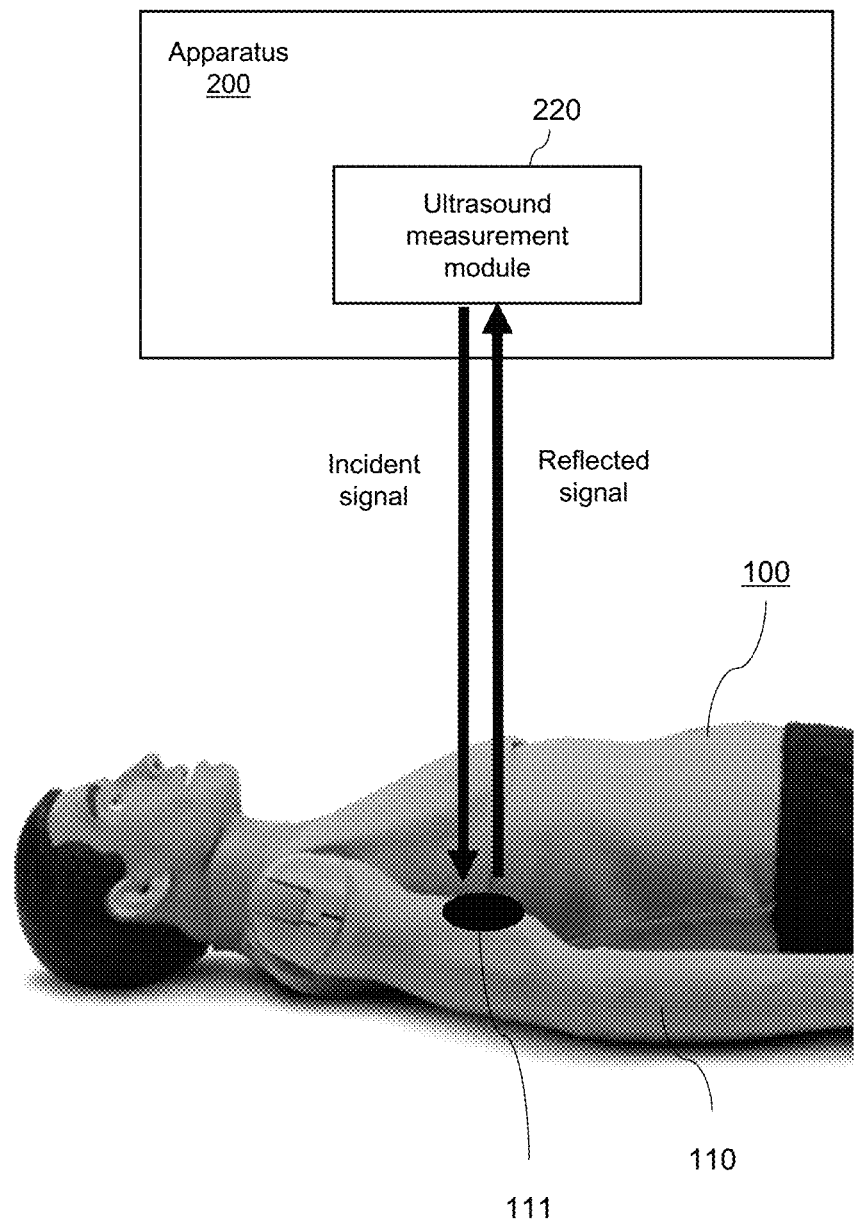
FIG. 3 illustrates operations of an ultrasound measurement module of the system represented in FIG. 1.

Reference is now made concurrently to FIGS. 1 and 3. FIG. 3 illustrates the operations of the ultrasound measurement module 220 of the apparatus 200.

As mentioned with respect to FIG. 2 and for illustration purposes, the object 100 is either a human or a patient simulator used for simulation procedures, and the object 100 comprises an arm 110 represented in FIG. 3. When the apparatus 200 is located adjacent to different positions with respect to the arm 110, the ultrasound measurement module 220 measures different values of an ultrasound characteristic, which depend on the current position of the apparatus 200 with respect to the arm 110. Examples of measurable ultrasound characteristics comprise: delay between ultrasound transmission and ultrasound reception, density of the received ultrasound signal, distribution of the received ultrasound signal, pattern of the ultrasound signal, or any other known characteristics used in ultrasound technology.

Although not illustrated in FIG. 3, if the apparatus 200 is moved longitudinally along the arm 110 from one extremity (the hand) to the other extremity (the shoulder), the ultrasound characteristic measured by the ultrasound measurement module 220 takes different values in a manner similar to the one illustrated in FIG. 2 for the measured magnetic field value.

More generally, when the apparatus 200 is positioned adjacent to the area 111 of the surface of the object 100, the ultrasound measurement module 220 generates an incident ultrasound signal, and the area 111 generates a corresponding reflected ultrasound signal received by the ultrasound measurement module 220. The ultrasound measurement module 220 measures the reflected ultrasound signal received by the ultrasound measurement module 220 and extracts therefrom values for ultrasound characteristic(s). The value(s) of the ultrasound characteristic(s) correspond(s) to the area 111 of the surface of the object 100. The orientation of the apparatus 200, as well as the distance between the apparatus 200 and the area 111 of the surface of the object 100, may vary. FIG. 3 is a schematic representation of the apparatus 200, and the size of the apparatus 200 with respect to the size of the arm 110 is not realistic.

Instead of being generated directly by the area 111 of the surface of the object 100, the reflected ultrasound signal may be generated by a region of the object 100 located inside the object 100. The region inside the object 100, the area 111 and the apparatus 200 are substantially aligned, so that the reflected ultrasound signal appears to have been generated by the area 111.

Ultrasound measurement modules 220 are well known in the art, and can have various form factors adapted for being integrated in various types of apparatus 200. The ultrasound measurement module 220 outputs value(s) of the measured ultrasound characteristic(s), which is(are) directly transmitted by the communication interface 230 of the apparatus 200. Alternatively, the ultrasound measurement module 220 outputs value(s) of the measured ultrasound characteristic(s), which is(are) processed (e.g. calibrated) before transmission by the communication interface 230 of the apparatus 200.

The magnetic field measurement module 210 and the ultrasound measurement module 220 are integrated in a single apparatus 200, so that they both provide a measurement corresponding to the same area 111 of the surface of the object 100. In a particular implementation mentioned previously, the apparatus 200 is an ultrasound device including by default the ultrasound measurement module 220, and adapted to also include the magnetic field measurement module 210.

Figure 4A:
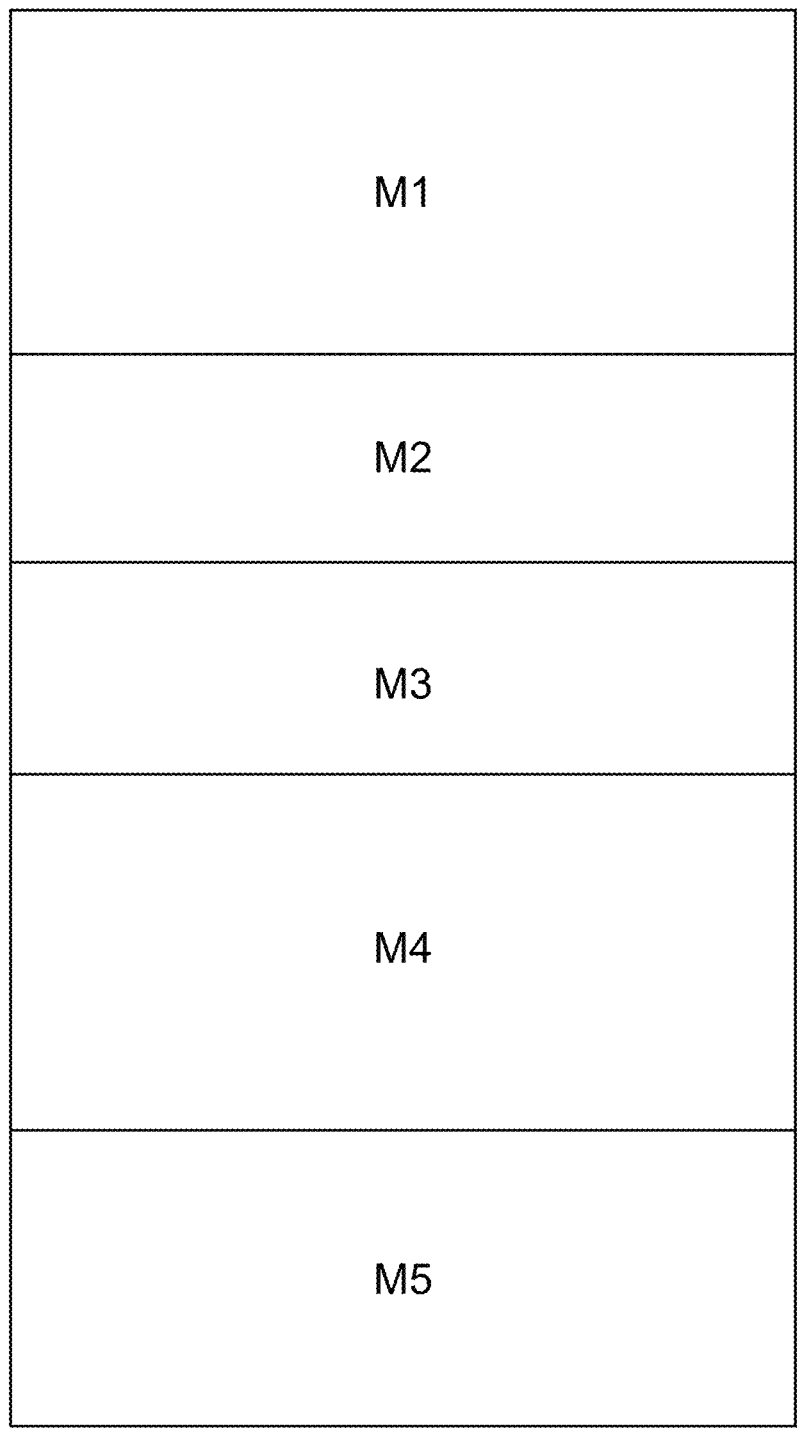
FIGS. 4A, 4B and 4C respectively illustrate a magnetic field map of the object represented in FIG. 1, an ultrasound map of the object represented in FIG. 1, and a combination of the magnetic field and ultrasound maps of FIGS. 4A and 4B.

Reference is now made concurrently to FIGS. 1, 4A, 4B and 4C. FIG. 4A represents a magnetic field map of the external surface of the object 100. The magnetic field map comprises a first plurality of reference areas of the external surface of the object 100. Each one of the first plurality of reference areas has an associated reference magnetic field value.

For illustration purposes, the magnetic field map represented in FIG. 4A corresponds to the upper external surface of the arm 110 represented in FIGS. 2 and 3. The illustrative magnetic field map comprises five reference areas M1, M2, M3, M4 and M5.

The magnetic field map comprising the first plurality of reference areas and the associated reference magnetic field values are determined during an initialization phase, and stored in the memory 320 of the control unit 300.

The determination of the magnetic field map may be implemented through various procedures. For instance, a magnetic field measurement device (e.g. the apparatus 200 or a dedicated magnetic field measurement apparatus different from the apparatus 200) is used in conjunction with an imaging apparatus for generating an image of the external surface of the object 100, and measuring an average magnetic field value for various areas of the external surface of the object 100. A data structure representing the magnetic field map is generated by the processing unit 310 of the control unit 300 based on the generated image of the external surface of the object 100, and stored in the memory 320. A user (e.g. a trainer or a technician) of the control unit 300 is involved in the process of generating the magnetic field map (via a user interface of the control unit 300 not represented in FIG. 1). The user divides the generated image of the external surface of the object 100 in a plurality of zones of interest, which consist of the first plurality of reference areas stored in the memory 320. For each one of the plurality of zones of interest, the user associates the average value of the measured magnetic field of the zone, which consists of the reference magnetic field stored in the memory 320. Alternatively, the user interacts with an independent computing device (not represented in FIG. 1) for generating the magnetic field map, which is transmitted from the independent computing device to the control apparatus 300, for storage in the memory 320. In addition to associating the average value of the measured magnetic field of the zone, the user may further store the gradient of the measured magnetic field upon displacement over each one of the plurality of zones of interest. Alternatively or concurrently, mathematical modeling may be used to evaluate the magnetic field map based on the conception information of the patient simulator.

The magnetic field map encompasses the entire external surface of the object 100. Alternatively, the magnetic field map only encompasses a portion of the external surface of the object 100, for instance the zones of interest identified by the user. The plurality of reference areas of the magnetic field map corresponds to organ(s), bone(s), blood vessel(s), etc., which are relevant for simulating one or more medical procedures.

Figure 4B:
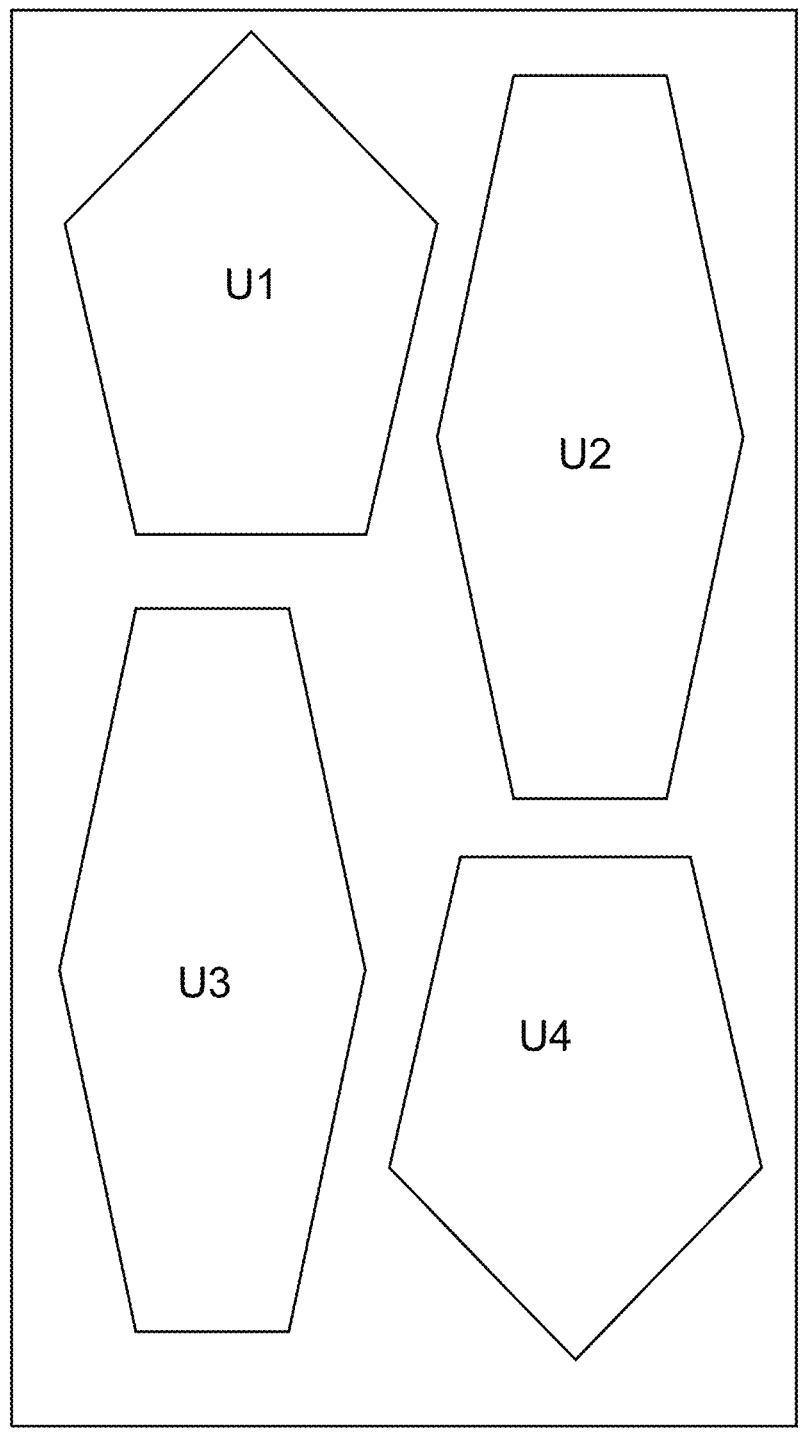

FIG. 4B represents an ultrasound map of the external surface of the object 100. The ultrasound map comprises a second plurality of reference areas of the external surface of the object 100. Each one of the second plurality of reference areas has an associated reference ultrasound characteristic.

For illustration purposes, the ultrasound map represented in FIG. 4B corresponds to the upper external surface of the arm 110 represented in FIGS. 2 and 3. The illustrative ultrasound map comprises four reference areas U1, U2, U3 and U4.

The ultrasound map comprising the second plurality of reference areas and the associated reference ultrasound characteristics are also determined during the initialization phase, and stored in the memory 320 of the control unit 300.

The determination of the ultrasound map may be implemented through various procedures. For instance, in a manner similar to the determination of the magnetic field map, an ultrasound measurement device (e.g. the apparatus 200 or a dedicated ultrasound measurement apparatus different from the apparatus 200) is used in conjunction with an imaging apparatus for generating an image of the external surface of the object 100, and measuring an average value of the ultrasound characteristic for various areas of the external surface of the object 100. A data structure representing the ultrasound map is generated by the processing unit 310 of the control unit 300 based on the generated image of the external surface of the object 100, and stored in the memory 320. A user (e.g. a trainer or a technician) of the control unit 300 is involved in the process of generating the ultrasound map (via a user interface of the control unit 300 not represented in FIG. 1). The user divides the generated image of the external surface of the object 100 in another plurality of zones of interest, which consist of the second plurality of reference areas stored in the memory 320. For each one of the second plurality of zones of interest, the user associates the average measured value of ultrasound characteristic (value, pattern, and/or gradient) of the zone, which consists of the reference ultrasound characteristic stored in the memory 320. Alternatively, the user interacts with an independent computing device (not represented in FIG. 1) for generating the ultrasound map, which is transmitted from the independent computing device to the control apparatus 300, for storage in the memory 320. Alternatively or concurrently, mathematical modeling may be used to evaluate the ultrasound field map based on the conception information of the patient simulator.

The ultrasound map encompasses the entire external surface of the object 100. Alternatively, the ultrasound map only encompasses a portion of the external surface of the object 100, for instance the zones of interest identified by the user. The plurality of reference areas of the ultrasound map also corresponds to organ(s), bone(s), blood vessel(s), etc., which are relevant for simulating the one or more medical procedures.

Figure 4C:
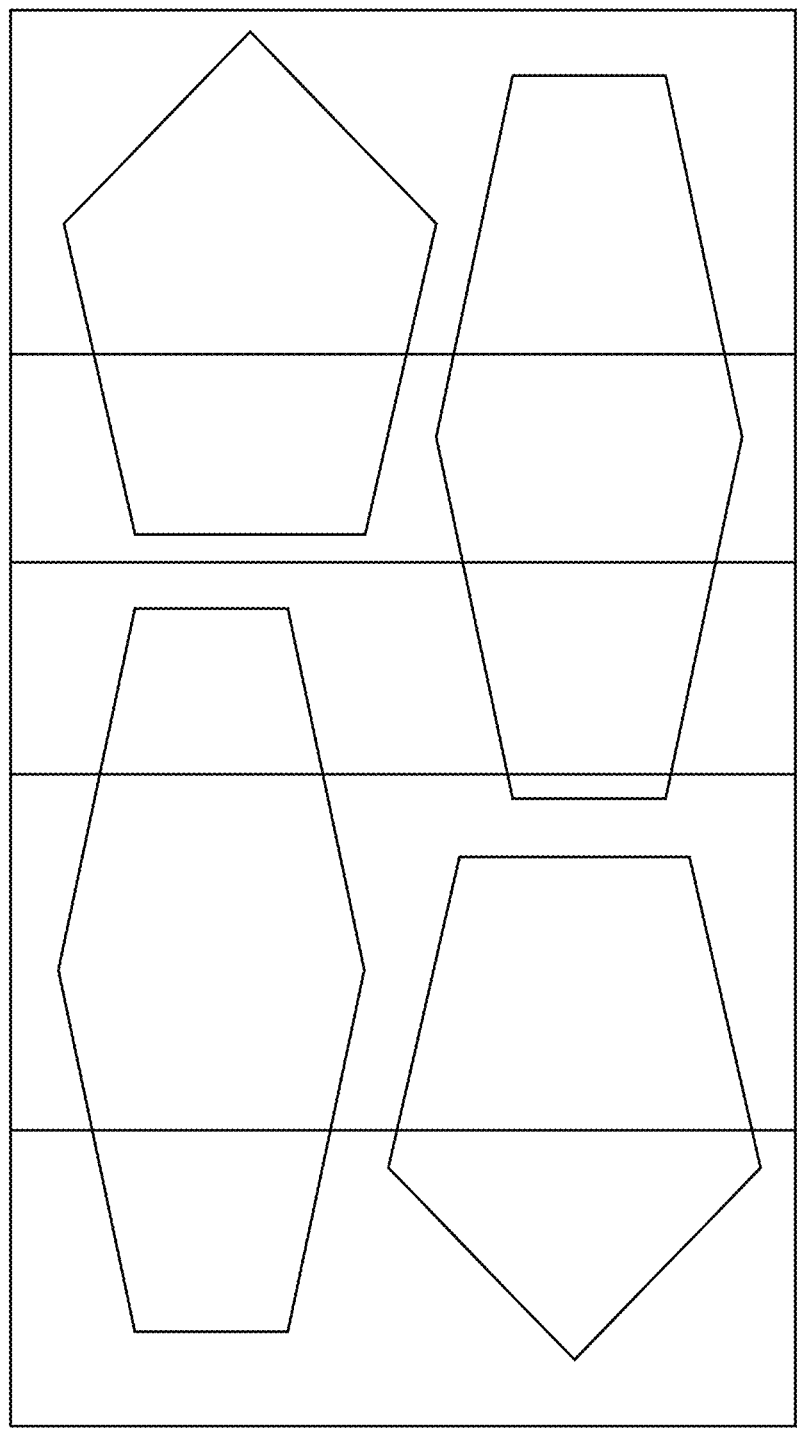

FIG. 4C represents an overlap of the magnetic field map of the external surface of the object 100 represented in FIG. 4B and the ultrasound map of the external surface of the object 100 represented in FIG. 4C. FIG. 4C illustrates the overlapping of the first plurality of reference areas of the magnetic field map with the second plurality of reference areas of the ultrasound map.

Reference is now made concurrently to FIGS. 1, 5A, 5B, 5C and 5D, which illustrate the determination of a position on the external surface of the object.

Upon reception of a measured magnetic field value (generated or induced by the magnetic field measurement module 210) through the communication interface 330 of the control unit 300, the processing unit 310 determines a subset of the first plurality of reference areas (of the magnetic field map) for which the associated reference magnetic field is substantially equal to the measured magnetic field value.

Figure 5A:
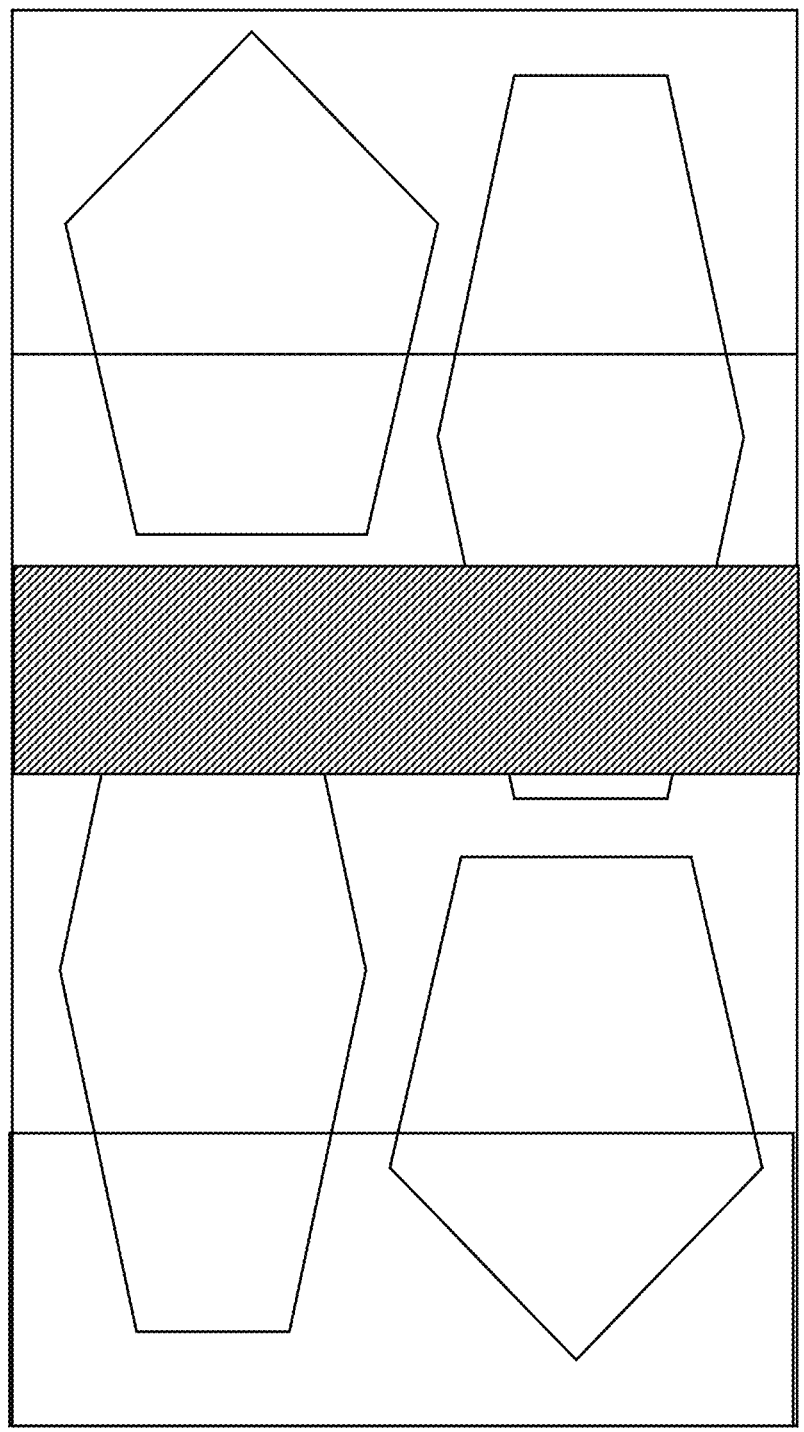
FIGS. 5A, 5B, 5C and 5D illustrate the determination by the system of FIG. 1 of the position on the external surface of the object of FIG. 1.

For illustration purposes, in FIG. 5A, a single reference area M3 of the magnetic field map has been determined. The determined subset of the first plurality of reference areas (of the magnetic field map) may include one or more areas.

A configurable tolerance margin can be used for determining the subset of the first plurality of refence areas. For example, if the measured magnetic field value is between 90% and 110% of a reference magnetic field, then the associated reference area is selected.

Upon reception of a measured ultrasound characteristic (generated by the ultrasound measurement module 220) through the communication interface 330 of the control unit 300, the processing unit 310 determines a subset of the second plurality of reference areas (of the ultrasound map) for which the associated reference ultrasound characteristic is substantially equal to the measured ultrasound characteristic.

Figure 5B:
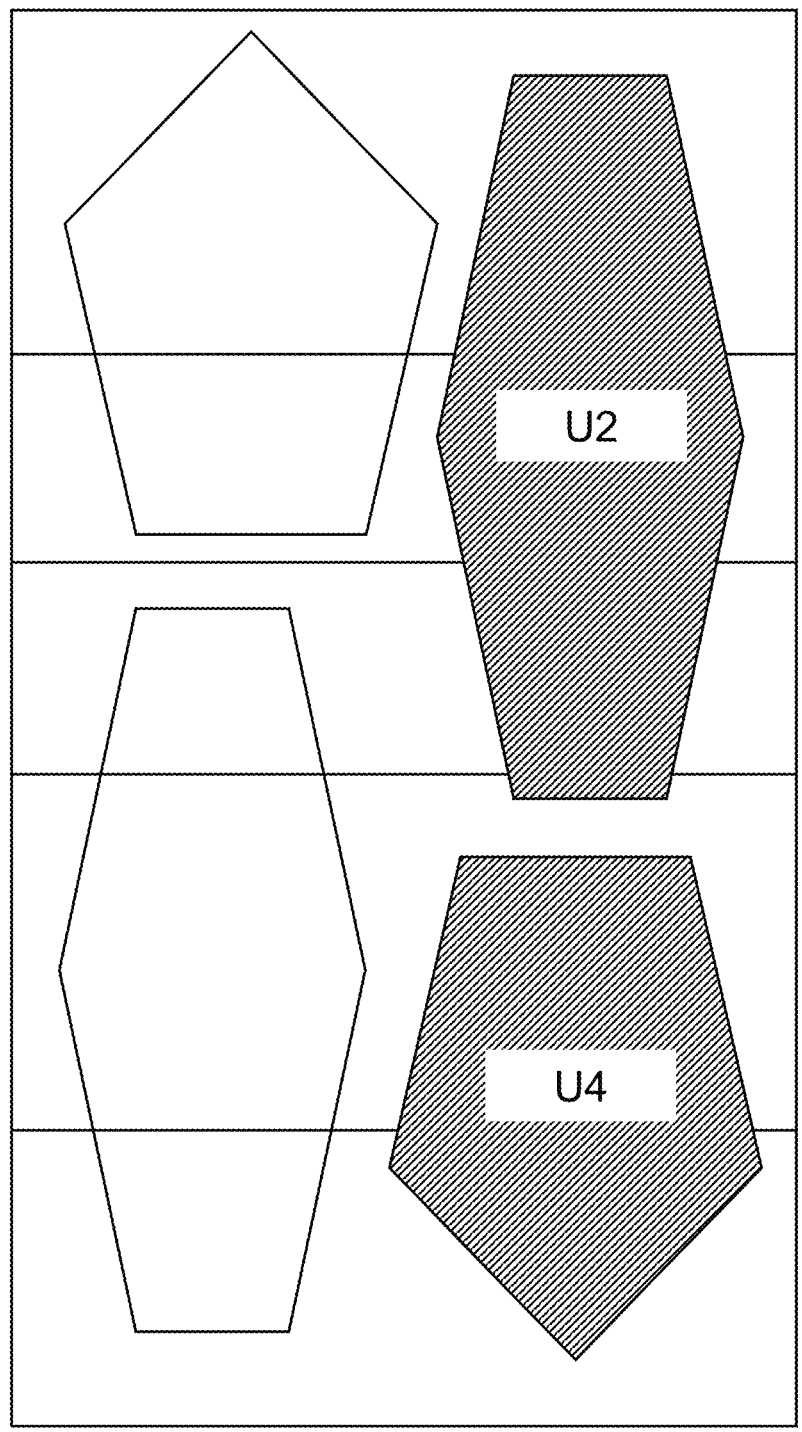

For illustration purposes, in FIG. 5B, two reference areas U2 and U4 of the ultrasound map have been determined. The determined subset of the second plurality of reference areas (of the ultrasound map) may include one or more areas.

A configurable tolerance margin can also be used for determining the subset of the second plurality of refence areas (which can be different from the one used for the magnetic field map). For example, if the measured ultrasound characteristic is between 95% and 105% of a reference ultrasound characteristic, then the associated reference area is selected.

The position on the external surface of the object 100 is determined by the processing unit 310 by correlating the subset of the first plurality of reference areas (of the magnetic field map) and the subset of the second plurality of reference areas (of the ultrasound map).

Figure 5C:
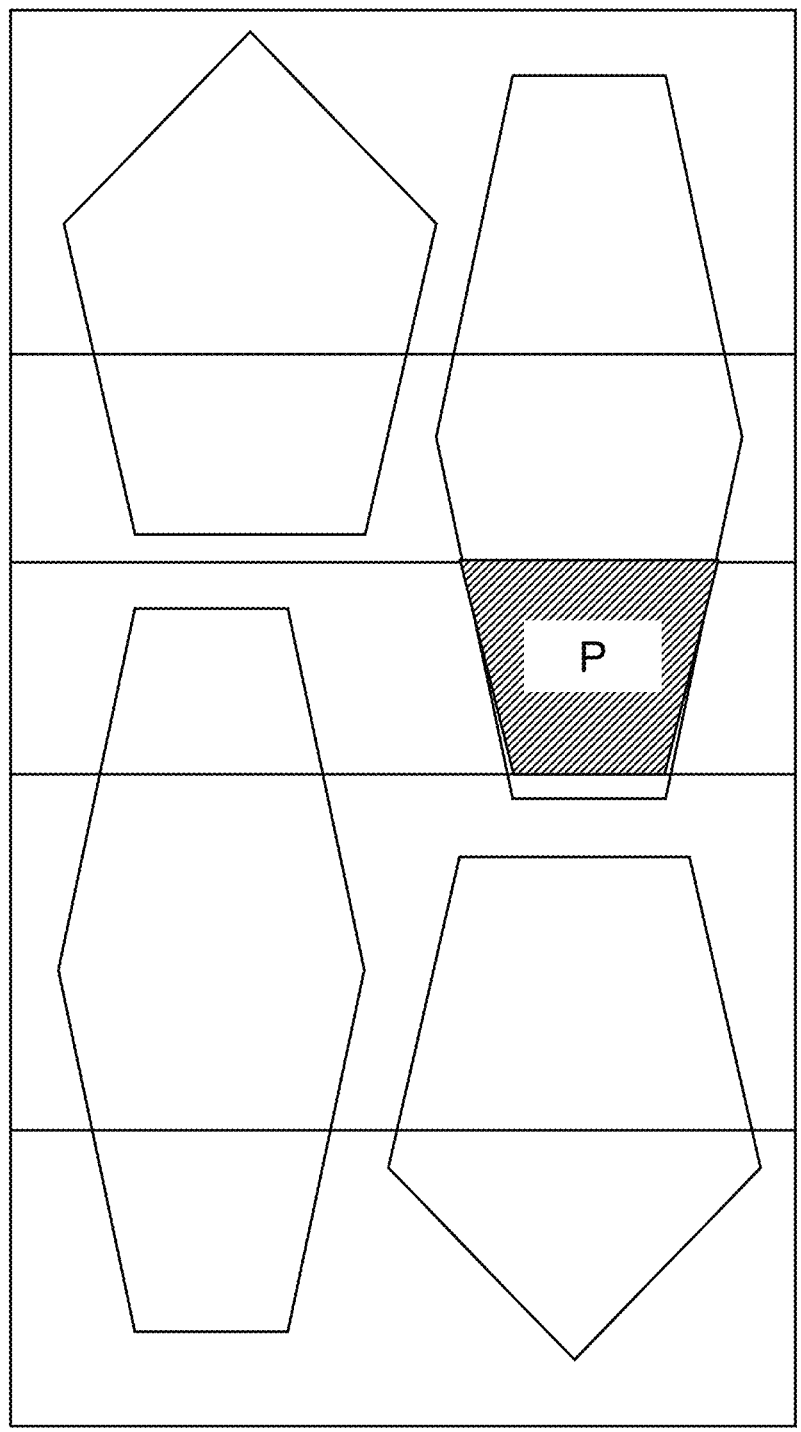

For illustration purposes, in FIG. 5C, one position P has been determined. However, based on the configurations of the magnetic field map and ultrasound map, for a given couple of measured magnetic field value and measured ultrasound characteristic, zero or one position may be determined. For example, if the determined magnetic reference area is M2 and the determined ultrasound reference area is U3, then no position can be determined.

The control unit 300 may store a 2D or 3D representation of the object 100 in memory 320. Upon determination of the position on the external surface of the object 100, the processing unit 310 displays on the display 340 a representation of the determined position on the 2D or 3D representation of the object 100.

Figure 5D:
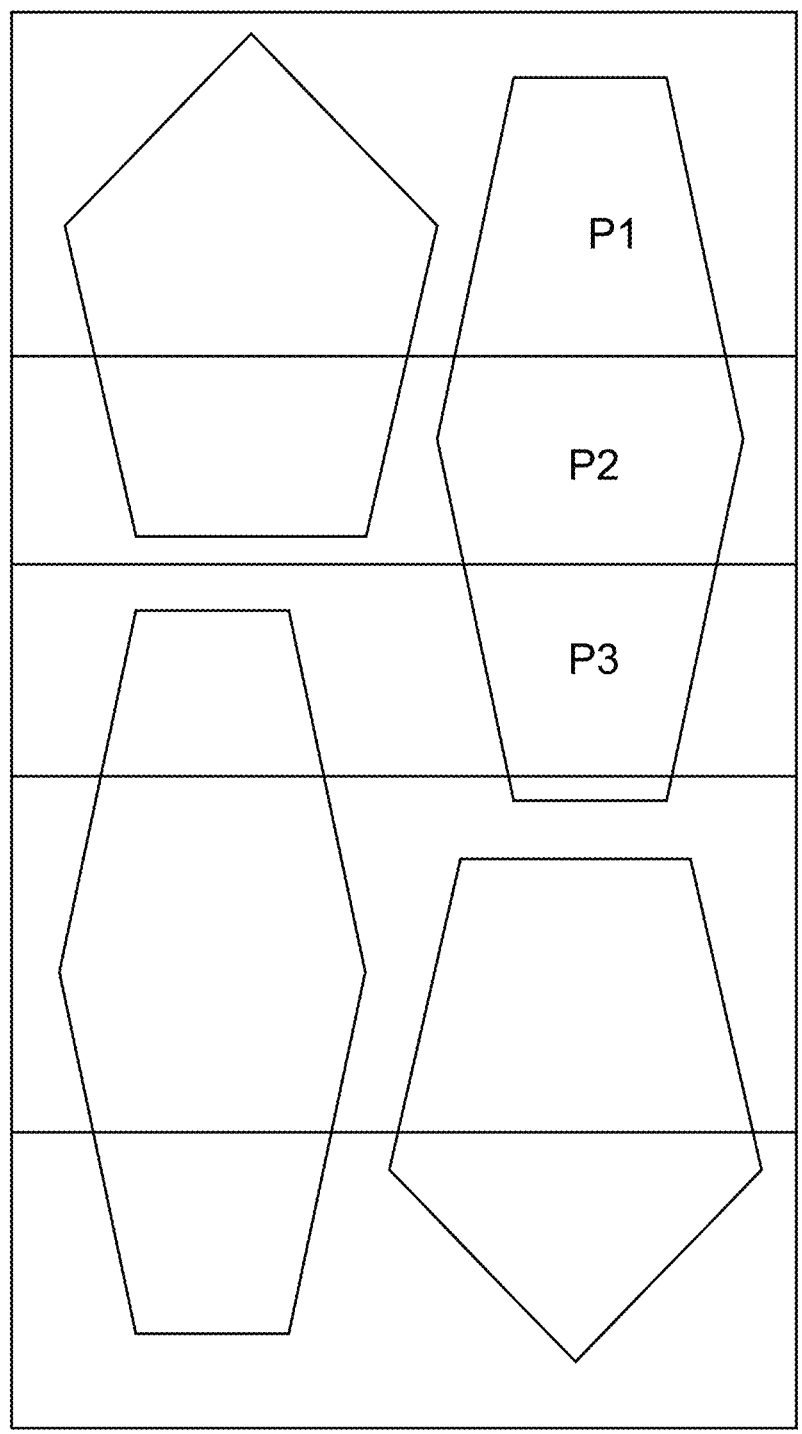

The determined position on the external surface of the object 100 is used for estimating the effective position of the apparatus 200 with respect to the external surface of the object 100. It can also be used for tracking a movement of the apparatus 200 along the external surface of the object 100. For example, as illustrated in FIG. 5D, the determined position on the external surface of the object 100 moves from position P1, to position P2, to position P3, in relation to a corresponding movement of the apparatus 200 along the external surface of the object 100.

Figure 6A:
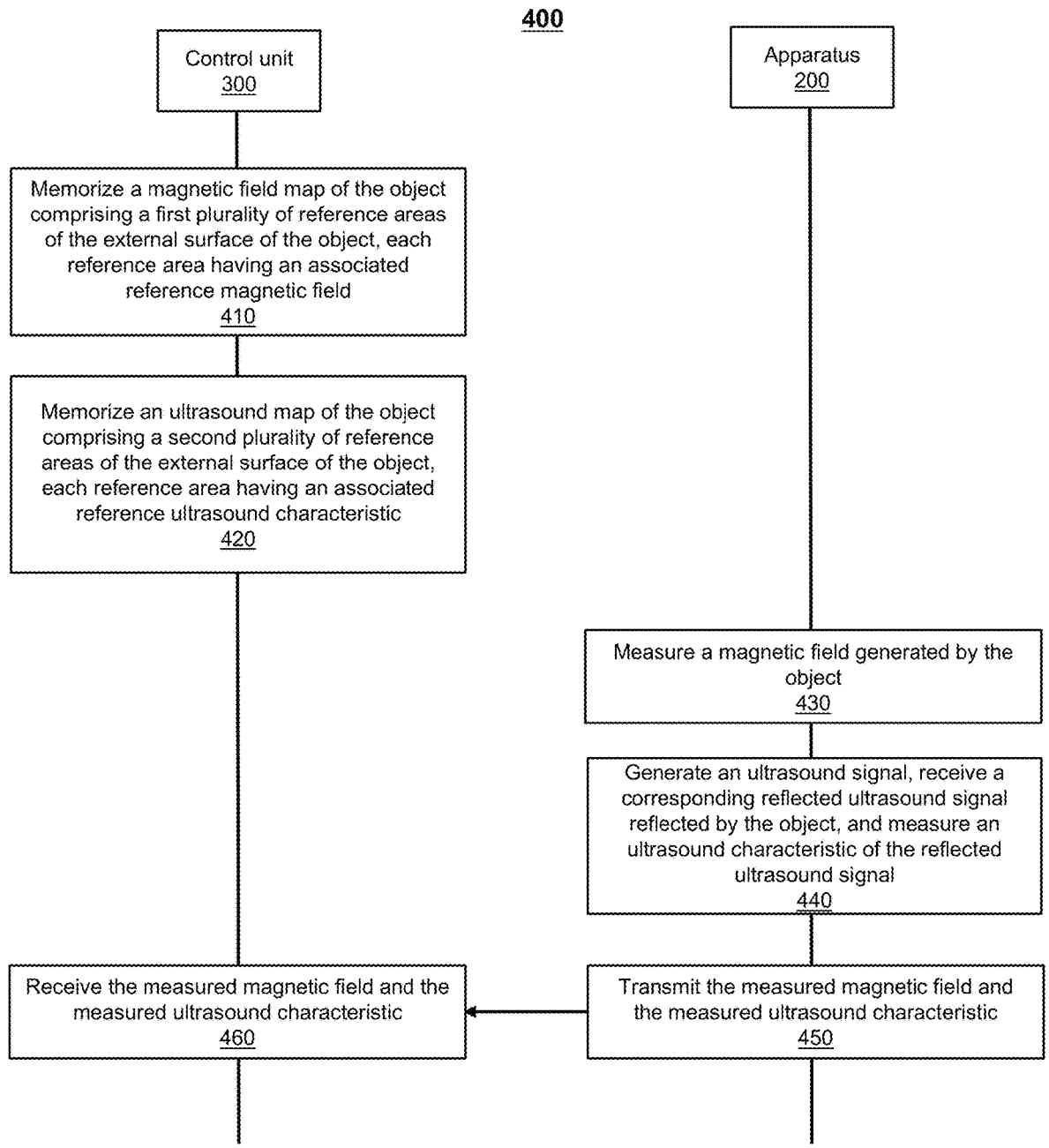
FIGS. 6A and 6B illustrate a method for determining a position on an external surface of an object.
Figure 6B:
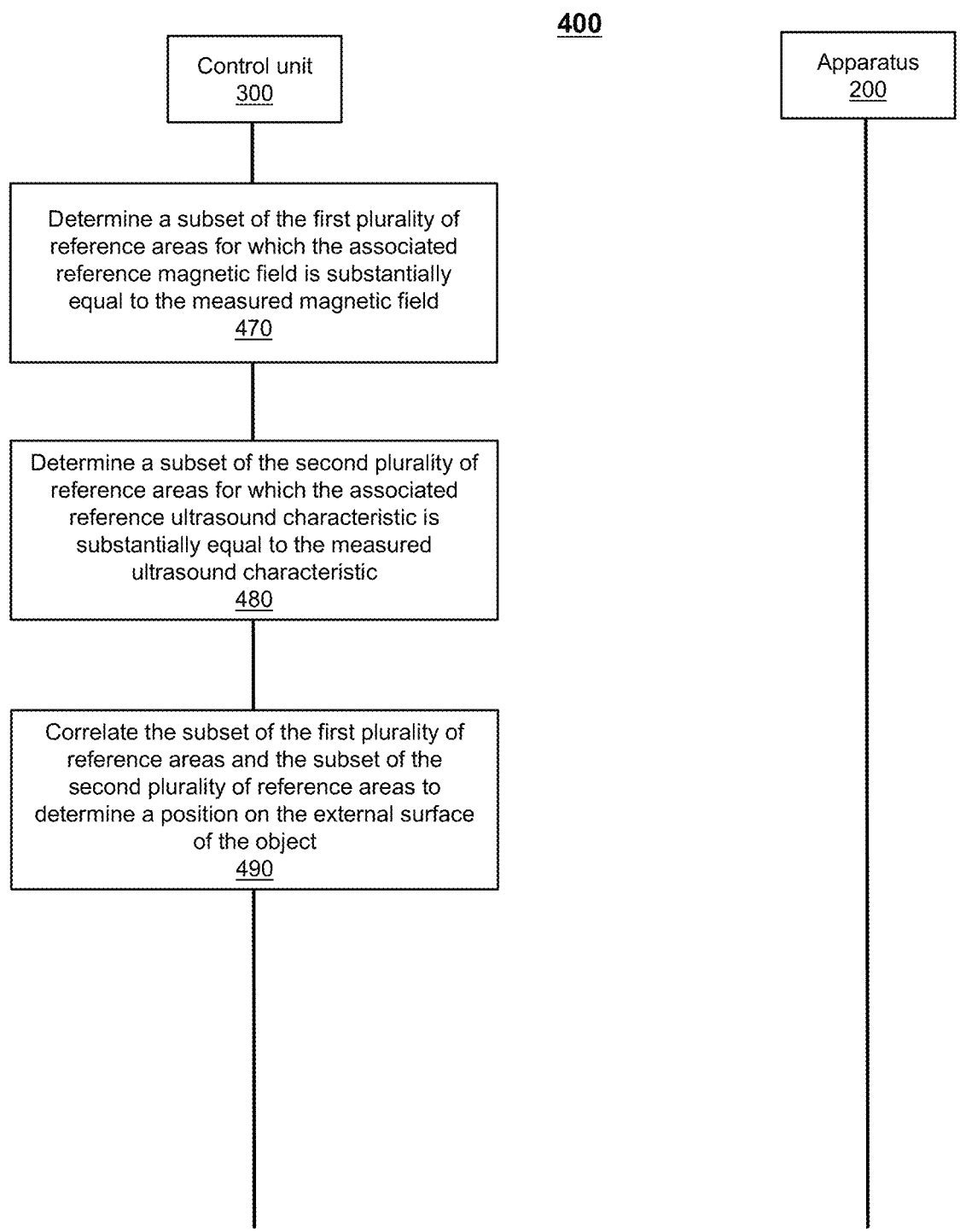

Referring now concurrently to FIGS. 1, 6A and 6B, a method 400 for determining a position on the external surface of the object 100 is represented in FIGS. 6A and 6B.

The steps of the method 400 include an initialization phase (steps 410 and 420) followed by an operational phase (steps 430 to 490), which have already been detailed in relation to the description of the system 10.

Step 410 of the method 400 consists in storing by the memory 320 of the control unit 300 the magnetic field map of the object 100. As mentioned previously, the magnetic field map comprises the first plurality of reference areas of the external surface of the object 100; and each one of the first plurality of reference areas has an associated reference magnetic field.

Step 420 of the method 400 consists in storing by the memory 320 of the control unit 300 the ultrasound map of the object 100. As mentioned previously, the ultrasound map comprises the second plurality of reference areas of the external surface of the object 100; and each one of the second plurality of reference areas has an associated reference ultrasound characteristic.

Step 430 of the method 400 consists in measuring by the magnetic field measurement module 210 of the apparatus 200 a magnetic field value generated or induced by the object 100.

Step 440 of the method 400 consists in generating by the ultrasound measurement module 220 of the apparatus 200 an ultrasound signal, receiving by the ultrasound measurement module 220 a corresponding reflected ultrasound signal reflected by the object 100, and measuring by the ultrasound measurement module 220 an ultrasound property of the reflected ultrasound signal.

Step 450 of the method 400 consists in transmitting by the communication interface 230 of the apparatus 200 the measured magnetic field value and the measured ultrasound characteristic to the control unit 300.

Step 460 of the method 400 consists in receiving by the communication interface 330 of the control unit 300 the measured magnetic field value and the measured ultrasound characteristic.

Step 470 of the method 400 consists in determining by the processing unit 310 of the control unit 300 a subset of the first plurality of reference areas (of the magnetic field map) for which the associated reference magnetic field is substantially equal to the measured magnetic field value.

Step 480 of the method 400 consists in determining by the processing unit 310 a subset of the second plurality of reference areas (of the ultrasound map) for which the associated reference ultrasound characteristic is substantially equal to the measured ultrasound characteristic.

Step 490 of the method 400 consists in correlating by the processing unit 310 the subset of the first plurality of reference areas (of the magnetic field map) and the subset of the second plurality of reference areas (of the ultrasound map) to determine a position on the external surface of the object 100.

Figure 7:
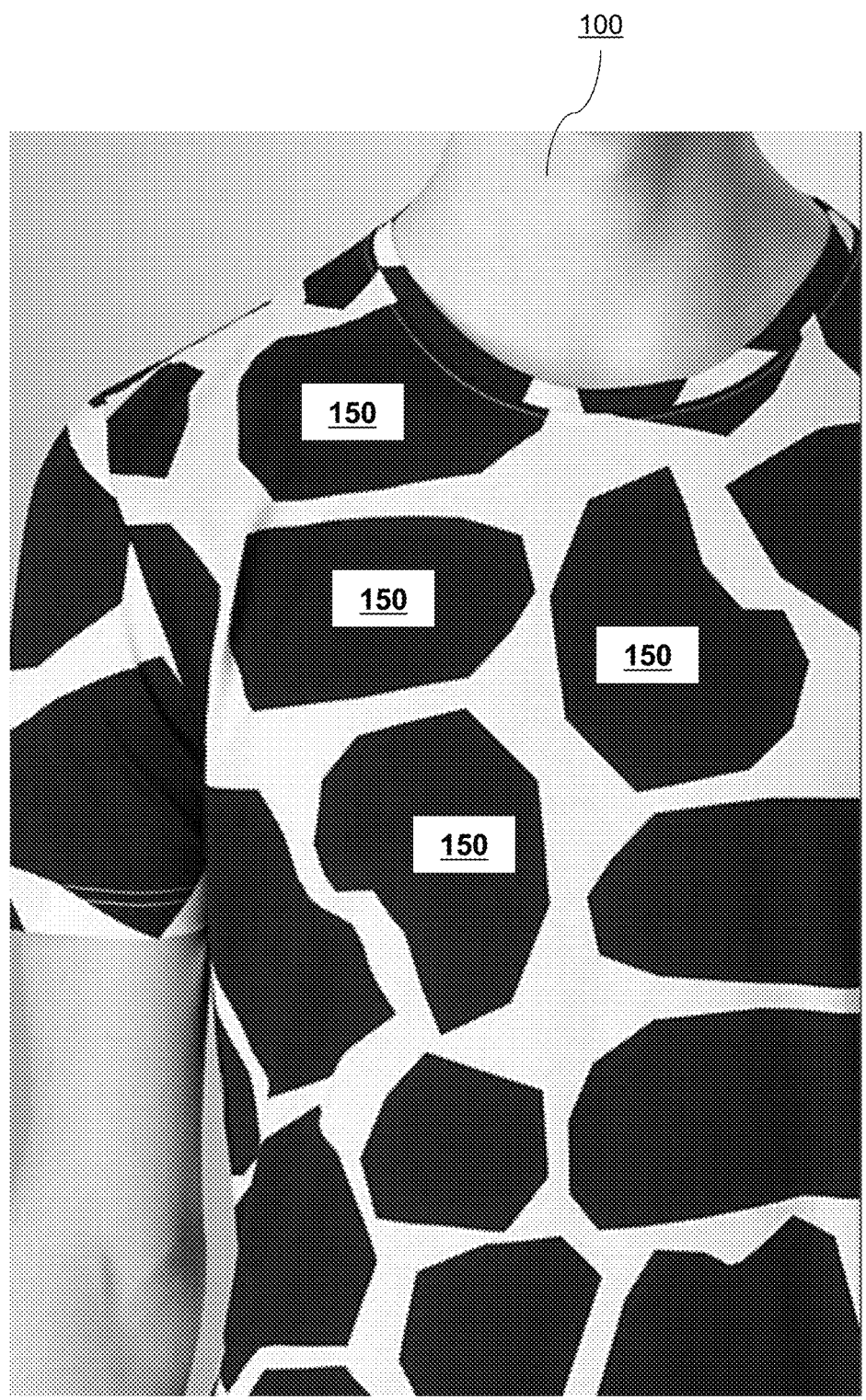
FIG. 7 illustrates a vest comprising a plurality of areas adapted for reflecting ultrasound signals.

Reference is now made concurrently to FIGS. 1 and 7. FIG. 7 represents a human wearing a vest. The vest includes a plurality of areas 150 adapted for reflecting the ultrasound signal generated by the ultrasound measurement module 220 of the apparatus 210. In the configuration represented in FIG. 7, the object 100 is the human wearing the vest. Alternatively, the object 100 is a patient simulator (simulating a human body) covered by the vest having the plurality of areas 150. The terminology vest shall be interpreted in a broad sense, to include any cloth wearable by a human or a patient simulator, and adapted to include the plurality of areas 150.

The plurality of areas 150 on the object 100 (the vest covering a human or a patient simulator) corresponds to the aforementioned second plurality of reference areas of the external surface of the object 100 which constitute the ultrasound map illustrated in FIG. 4B. Alternatively, the plurality of areas 150 could concurrently correspond to the first and second plurality of reference areas of the external surface of the object 100, which constitute the magnetic map and the ultrasound map.

An ultrasound reflective material (e.g. an ink, a polymer, an alloy, etc.) is applied to each area 150 of the vest. For each area 150, a density of the ultrasound reflective material is varied within the area 150, in such a manner that the density of the ultrasound reflective material on the surface of the area 150 varies according to a known pattern. Alternatively or complementarily, for each area 150, two-dimensional (2D) or three-dimensional (3D) shapes are created with the ultrasound reflective material within the area 150, in such a manner that the 2D or 3D shapes on the surface of the area 150 vary according to a known pattern. In the event where the areas 150 concurrently correspond to the first and second plurality of reference areas, at least one area 150 of the object further generates or induces a magnetic field which may be measured by the magnetic field measurement module 210.

The ultrasound measurement module 220 of the apparatus 200 generates ultrasound images of sub-areas of an area 150 of the vest, when the apparatus 200 is adjacent to the area 150 and moves within range of the area 150. The ultrasound images of the sub-areas are transmitted to the control unit 300 and analyzed by the processing unit 310 of the control unit 300. The ultrasound images of the sub-areas have identifiable properties, due to the density variation and/or shape variation of the ultrasound reflective material on the surface of the area 150. By analyzing these specific properties, the processing unit 310 determines at least one of the following: a position within the area 150 corresponding to a current position of the apparatus 200, an orientation of the apparatus 200, etc.

Since the material structure of each area 150 covered by the ultrasound reflective material is similar, it may not always be possible to distinguish one area 150 from another area 150, based on the collected ultrasound images of the sub-areas of the areas 150. Thus, the aforementioned magnetic field map and ultrasound map are used as described previously and illustrated in FIGS. 5A, 5B and 5C, to identify one area 150 among the plurality of areas 150 being currently adjacent to the apparatus 200.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A system for determining a position on an external surface of an object, the system comprising:
   an apparatus comprising:
      a magnetic field measurement module for measuring a magnetic field value induced by the object;
      an ultrasound measurement module for generating an ultrasound signal, receiving a corresponding reflected ultrasound signal reflected by the object, and measuring an ultrasound characteristic of the reflected ultrasound signal; and
   a control unit comprising:
   memory for storing:
      a magnetic field map of the object, the magnetic field map comprising a first plurality of reference areas of the external surface of the object, each one of the first plurality of reference areas having an associated reference magnetic field value, and an ultrasound map of the object, the ultrasound map comprising a second plurality of reference areas of the external surface of the object, each one of the second plurality of reference areas having an associated reference ultrasound characteristic;
   a processing unit for:
      determining a subset of the first plurality of reference areas for which the associated reference magnetic field value is substantially equal to the measured magnetic field value;
      determining a subset of the second plurality of reference areas for which the associated reference ultrasound characteristic is substantially equal to the measured ultrasound characteristic; and
      correlating the subset of the first plurality of reference areas and the subset of the second plurality of reference areas to determine the position on the external surface of the object.

2. The system of claim 1, wherein the measured ultrasound characteristic comprises at least one of the following: delay of receipt of the reflected ultrasound signal, a gradient of the reflected ultrasound signal, and a pattern of the reflected ultrasound signal.

3. The system of claim 1, wherein the object is a patient simulator for simulating medical procedures.

4. The system of claim 1, wherein the apparatus is a simulator of a medical instrument.

5. The system of claim 1, wherein the control unit further comprises a display for displaying a representation of the object and a representation of the determined position on the representation of the object.

6. The system of claim 1, further comprising the object, the object consisting of a vest or a patient simulator covered by a vest, the vest comprising a plurality of areas corresponding to the second plurality of reference areas of the external surface of the object, the plurality of areas being adapted for reflecting the ultrasound signal generated by the ultrasound measurement module of the apparatus.

7. A method for determining a position on an external surface of an object, the method comprising:
   storing by a memory of a control unit a magnetic field map of the object, the magnetic field map comprising a first plurality of reference areas of the external surface of the object, each one of the first plurality of reference areas having an associated reference magnetic field value;
   storing by the memory of the control unit an ultrasound map of the object, the ultrasound map comprising a second plurality of reference areas of the external surface of the object, each one of the second plurality of reference areas having an associated reference ultrasound characteristic;
   measuring by a magnetic field measurement module of an apparatus a magnetic field value induced by the object;
   generating by an ultrasound measurement module of the apparatus an ultrasound signal;
   receiving by the ultrasound measurement module of the apparatus a corresponding reflected ultrasound signal reflected by the object;
   measuring by the ultrasound measurement module of the apparatus an ultrasound characteristic of the reflected ultrasound signal;
   transmitting by a communication interface of the apparatus the measured magnetic field value and the measured ultrasound characteristic to the control unit;
   receiving by a communication interface of the control unit the measured magnetic field value and the measured ultrasound characteristic;
   determining by a processing unit of the control unit a subset of the first plurality of reference areas for which the associated reference magnetic field value is substantially equal to the measured magnetic field value;
   determining by the processing unit of the control unit a subset of the second plurality of reference areas for which the associated reference ultrasound characteristic is substantially equal to the measured ultrasound characteristic; and
   correlating by the processing unit of the control unit the subset of the first plurality of reference areas and the subset of the second plurality of reference areas to determine the position on the external surface of the object.

8. The method of claim 7, wherein the measured ultrasound characteristic comprises at least one of the following: delay of receipt of the reflected ultrasound signal, a gradient of the reflected ultrasound signal, and a pattern of the reflected ultrasound signal.

9. The method of claim 8, wherein the object is a patient simulator for simulating medical procedures.

10. The method of claim 8, wherein the apparatus is a simulator of a medical instrument.

11. The method of claim 8, wherein the control unit further comprises a display for displaying a representation of the object and a representation of the determined position on the representation of the object.

12. The method of claim 8, wherein the object consists of a vest or a patient simulator covered by a vest, the vest comprising a plurality of areas corresponding to the second plurality of reference areas of the external surface of the object, the plurality of areas being adapted for reflecting the ultrasound signal generated by the ultrasound measurement module of the apparatus.

\* \* \* \* \*